United States Patent [19]

Vilendrer

[11] Patent Number: 5,670,708

[45] Date of Patent: Sep. 23, 1997

[54] HIGH FREQUENCY INTRAVASCULAR PROSTHESIS FATIGUE TESTER

[75] Inventor: Kent Vilendrer, Eden Prairie, Minn.

[73] Assignee: Endura-Tec Systems Corporation, Eden Prairie, Minn.

[21] Appl. No.: 626,486

[22] Filed: Apr. 2, 1996

[51] Int. Cl.⁶ .................................................. G01M 19/00
[52] U.S. Cl. .................................................. 73/37; 73/866.4
[58] Field of Search .......................... 73/37, 865.6, 866.4

[56] References Cited

U.S. PATENT DOCUMENTS

| | | | |
|---|---|---|---|
| 2,754,677 | 7/1956 | New | 73/37 |
| 3,481,190 | 12/1969 | Inoue | 73/37 X |
| 3,610,031 | 10/1971 | Clark et al. | |
| 3,911,735 | 10/1975 | DiCrispino | 73/37 X |
| 4,381,663 | 5/1983 | Swanson | 73/37 |
| 4,546,642 | 10/1985 | Swanson | 73/37 |
| 4,972,721 | 11/1990 | Conti | 73/807 |
| 5,272,909 | 12/1993 | Nguyen et al. | 73/37 |
| 5,327,774 | 7/1994 | Nguyen et al. | 73/37 |
| 5,339,693 | 8/1994 | Rowlands et al. | 73/825 |
| 5,379,645 | 1/1995 | Smart | 73/794 |
| 5,406,857 | 4/1995 | Eberhardt et al. | 73/866.4 |
| 5,528,944 | 6/1996 | Hoyt et al. | 73/866.4 |

*Primary Examiner*—Thomas P. Noland
*Attorney, Agent, or Firm*—Haugen & Nikolai, PA

[57] ABSTRACT

A physiological simulation device for measuring compliance conditions of a prosthesis, such as stents, grafts and stent-grafts, under simulated physiologic loading conditions. The prosthesis is positioned within a fluid conduit of the fatigue tester, wherein the fluid conduit is filled with a saline solution or other fluid approximating the physiological condition to be tested. The fluids are forced through the fluid conduit from both ends of the fluid conduit in a pulsating fashion at a high frequency, thereby simulating systolic and diastolic pressures. The temperature of the fluid is maintained at a specific (37° C.) temperature via a closed loop PID control system. The fluids are pulsated by a pulse generation system consisting of a voice coil drive motor connected to a bellows assembly. Use of a linear drive motor increases the number of cycles per minute to which the prosthesis may be subjected. A microprocessor-based controller operates the pulse generation system at a frequency ranging from 0 to over 6000 cycles/minute under closed loop control. The microprocessor-based controller may be servo controlled, utilizing feedback from a compliance transducer system, linear displacement transducer, and pressure transducer.

11 Claims, 7 Drawing Sheets

HIGH FREQUENCY INTRAVASCULAR PROSTHESIS FATIGUE TESTER

BACKGROUND OF THE INVENTION

I. Field of the Invention

This invention relates generally to the field of bioprosthetic fatigue testing devices, and more particularly to an apparatus and method for testing in vitro, at an accelerated rate, the compliance conditions of bioprosthetic stent, graft, stent-grafts and other prosthesis, under simulated physiological loading conditions.

II. Discussion of the Related Art

In the past fatigue testers have been used to perform in vitro fatigue testing of various endovascular prosthesis such as stents, stent-grafts, grafts, and heart valves under simulated physiological loading conditions. Typically, these endovascular prosthesis are post amendment class III devices which require the approval of the Food & Drug Administration (FDA) from a PMA application prior to commercial marketing.

As part of the PMA application, the FDA requires medical device manufacturers of stents to submit clinical and in vitro test data to support the safety and efficacy of the permanent implant device. The stent guidelines for PMA submission require clinical study data and in vitro test data. One required in vitro test is the accelerated fatigue testing of a stent. The guidelines require 10 years equivalent of test data. This translates to 400 million cycles of fatigue stress.

The present fatigue testers force fluid within the lumen of a stent at a maximum pulse frequency ranging between 1000–2000 cycles per minute. In order to obtain the required test data with present fatigue testers, the testers must run continuously over a period of several months or even years. Hence, a need exists for a fatigue tester that is operable at a significantly higher frequency.

The present fatigue testers typically include a rotary motor and crank arrangement used to drive bellows and pulse the fluids. For example, Conti in U.S. Pat. No. 4,972,721 and Swanson in U.S. Pat. No. 4,381,663 both disclose a fatigue tester, teaching the use of a rotary motor and crank to thereby pulse or oscillate fluids within a container. The disclosed fatigue testers operate at a maximum pulse frequency ranging between 1000–2000 cycles per minute and are not servo controlled. Also, the '721 and '663 fatigue testers do not use information related to test chamber compliance for test control. Servo control of the fatigue tester would allow the user to more precisely control the fatigue testing of the prosthesis. Therefore, a need exists for a servo controlled fatigue tester that utilizes high frequency pumps, to thereby control the pressure, amplitude and frequency of the fluids forced into the fluid conduit containing the prosthesis. The present invention overcomes these and other disadvantages of the prior art.

SUMMARY OF THE INVENTION

The purpose of the present invention is to provide a fatigue tester for simulating physiologic loading conditions on a prosthesis. Fatigue testing of the prosthesis is performed by placing the prosthesis within a channel of an elastic fluid conduit filled with saline or other fluid, wherein the fatigue tester pulsates fluid into the channel from each end of the channel, to thereby simulate vessel compliance conditions (depending on the test protocol). By pulsating fluid into the channel from each end of the channel, the diameter of the fluid conduit and stent, for example, increases and decreases, thereby subjecting the prosthesis to fatigue stress/strains. At various intervals of the fatigue test, the prosthesis can be removed and examined under an SEM for mechanical integrity.

The in vitro fatigue test can be performed at simulated heart beat rates from 0–100 beats per second, fluid conduit or tube compliances from 0–7% and vessel pressures from 1–1000 mm Hg. The fatigue tester may test prosthesis such as stents, grafts and stent-grafts.

The fatigue tester generally includes a fluid conduit, linear driven pumps, linear displacement transducers, pressure and temperature transducers, a compliance transducer, and heating elements. The fatigue tester is coupled to a monitoring and control system including a microprocessor-based controller, microprocessor-based temperature controller and compliance controller to control by closed loop feedback the amplitude and frequency of fluid forced into the tubes. Those skilled in the art will appreciate that although the linear driven pumps and heating elements could be controlled manually, an automatic microprocessor-based controller is preferred.

The fluid conduit includes at least one elastic simulated arterial/venous tube which approximates the geometry of a healthy human arterial/venous vessel. In the preferred embodiment, each end of each tube is connected to a distribution manifold that is in-turn connected to a linear driven pump. Each linear driven pump includes a linear drive motor and attached bellows.

The linear drive motors are coupled to linear displacement transducers which are connected to the microprocessor-based controller. The microprocessor-based controller operates the linear driven pumps over a frequency range from 0 to over 6000 cycles/minute under closed loop control.

The tubes, distribution manifolds and bellows are filled with a saline solution or other fluid approximating physiological condition to be tested. The temperature of the fluid is maintained at a specific (37° C.) temperature via a closed loop PID control system. The PID control system includes a conventional temperature transducer and heating element coupled to both a microprocessor-based temperature controller and the fluid conduit.

The tube's radial dilation is measured via the compliance transducer which is coupled to the compliance controller. The compliance controller is coupled to the microprocessor-based controller. The resulting dilation of the tube can be mapped along the tube length by means of a precision linear sliding scale linked to the compliance measurement transducer. A signal corresponding to the resulting dilation is transmitted to the microprocessor-based controller for monitoring and control purposes and can be used to ensure that the test is run at a specific dilation range.

The pressure within the fluid conduit is measured via a pressure transducer. The pressure is monitored by the microprocessor-based controller and used as part of the closed loop servo control. To ensure long term test reliability, an uninterruptable power supply is connected to the microprocessor-based controller. The uninterruptable power supply is controlled by the microprocessor-based controller including an automatic data storage and initialization of a predefined shutdown sequence on power outage.

OBJECTS

It is accordingly a principal object of the present invention to provide a high frequency linear driven fatigue tester for simulating physiologic loading conditions on a prosthesis.

Another object of the present invention is to provide a servo controlled fatigue tester, wherein the amplitude and frequency of fluid, forced into channels retaining the prosthesis, is controlled by closed loop feedback.

Still another object of the present invention is to provide a high frequency linear driven fatigue tester that includes linear driven pumps which operate over a frequency range from 0 to over 6000 cycles/minute.

These and other objects, as well as these and other features and advantages of the present invention will become readily apparent to those skilled in the art from a review of the following detailed description of the preferred embodiment in conjunction with the accompanying drawings and claims, in which like numerals in the several views refer to corresponding parts.

DETAILED DESCRIPTION OF THE PREFERRED EMBODIMENT

Figure 1:
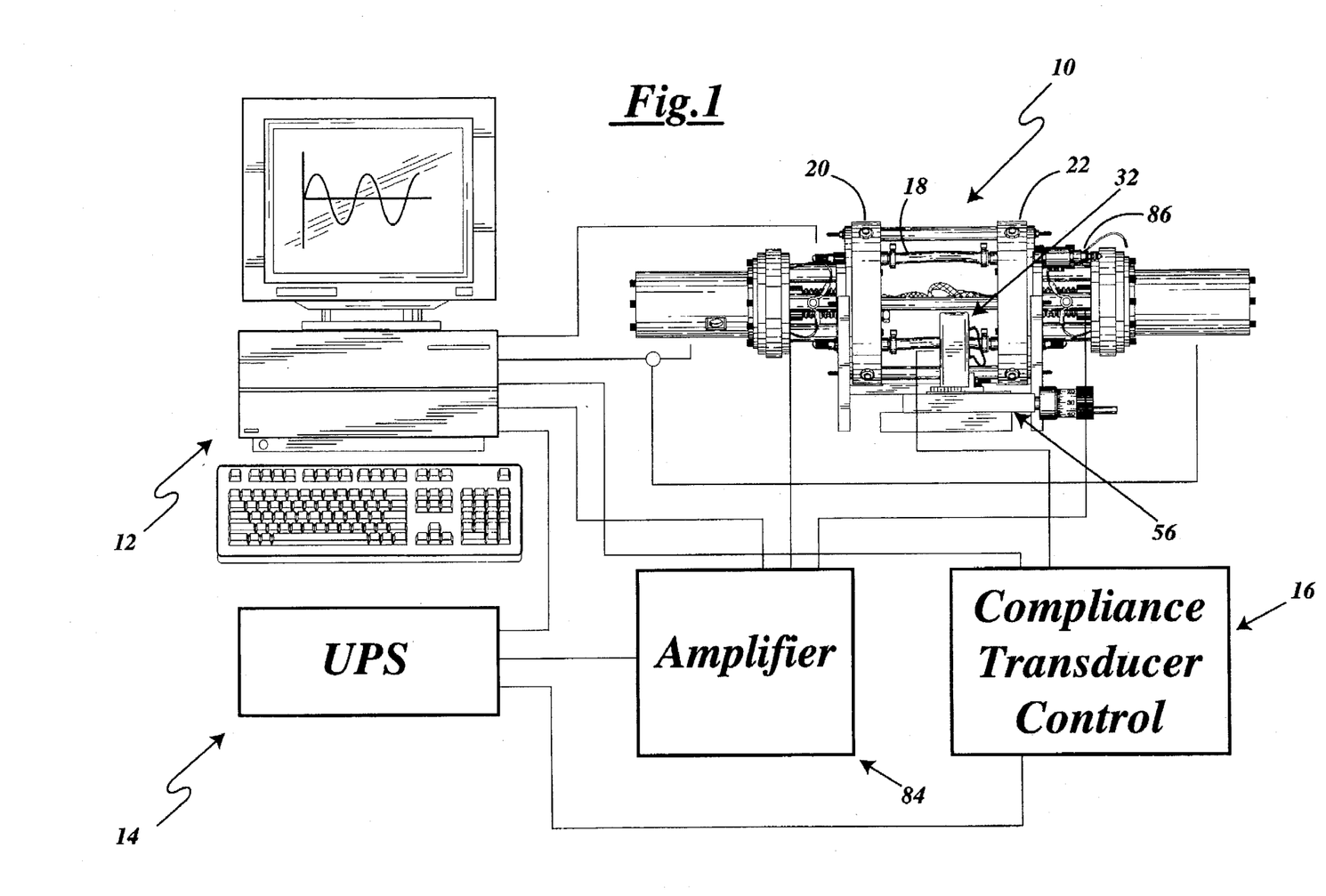
FIG. 1 is a partial block diagram view showing the intravascular prosthesis fatigue tester connected to the monitoring and control system.

Referring first to FIG. 1, there is shown generally a fatigue tester 10 connected to a microprocessor-based controller 12, an uninterruptable power supply 14, and a compliance transducer controller 16. The fatigue tester 10 generally includes a plurality of prosthesis containing tubes 18, manifolds 20 and 22, bellows 24 and 26 and linear voice-coil drive motors 28 and 30.

A plurality of transducers, including a compliance transducer 32, temperature transducer 34, pressure transducer 38, and linear displacement transducers 40 and 42 are coupled to the fatigue tester 10. The pressure transducer 38, and linear displacement transducers 40 and 42 are also coupled to the microprocessor-based controller 12 (see FIGS. 1, 2 and 5) to provide feedback for closed loop servo control.

Figure 2:
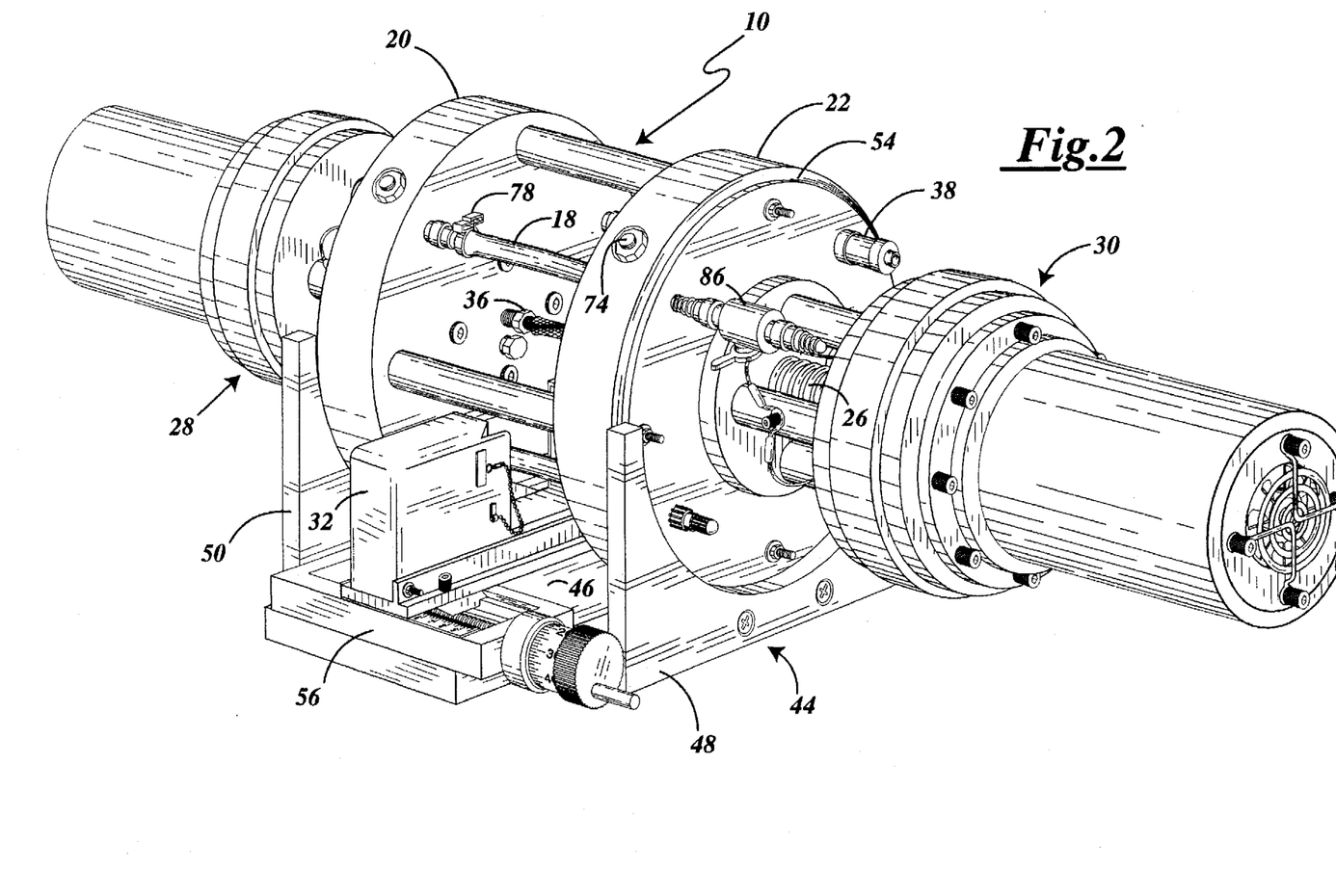
FIG. 2 is a front perspective view of the intravascular prosthesis fatigue tester with electrical wiring removed for clarity.

The fatigue tester 10 is placed on support member 44 (see FIG. 2). The support member 44 has a base 46 and fore and aft supports 48 and 50. Shoulders 52 and 54 of manifolds 20 and 22 respectively rest on support members 48 and 50, whereby the engaged shoulders 52 and 54 align and position the fatigue tester 10 relative to the support member 44.

Figure 4:
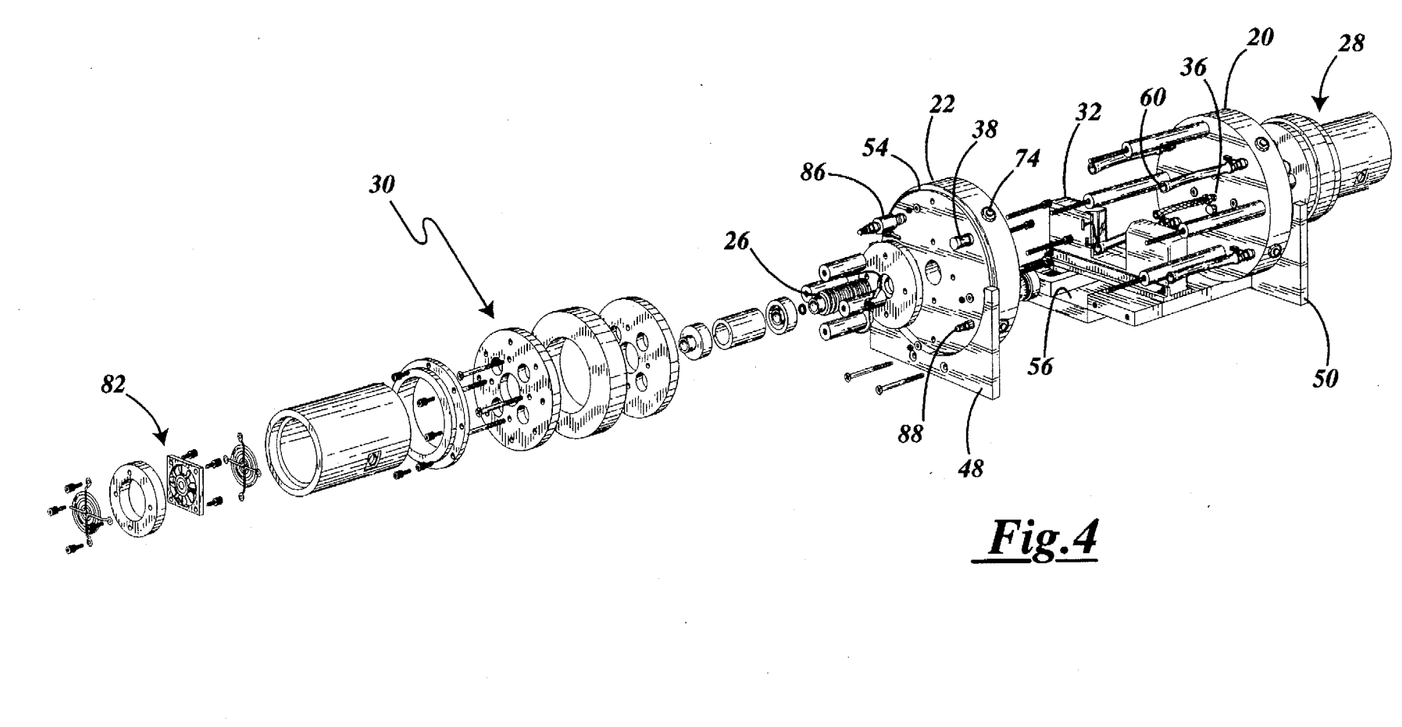
FIG. 4 is a partially exploded back perspective view of the intravascular prosthesis fatigue tester of the type shown in FIG. 2, with the linear drive transducer removed for clarity.
Figure 7:
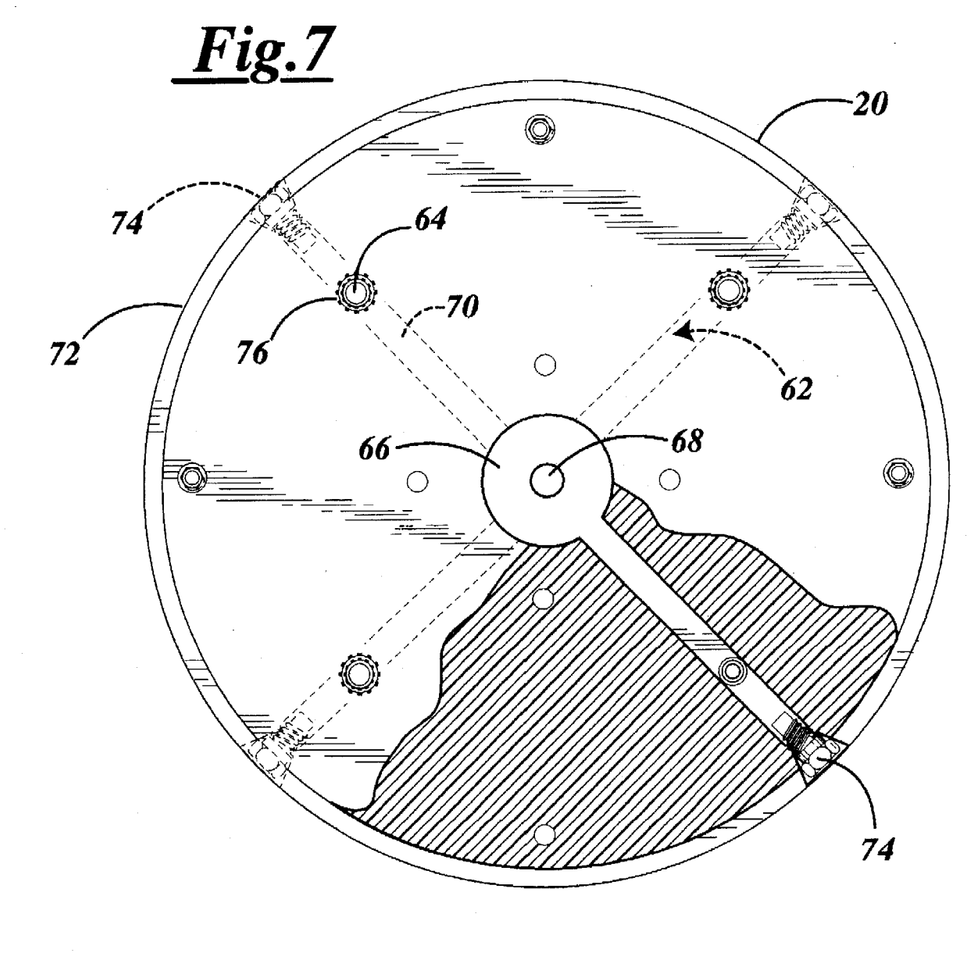
FIG. 7 is a partial sectional end view of the manifold of the type shown in FIG. 2 removed from the fatigue tester.

In the preferred embodiment, the manifolds 20 and 22 are cylindrical in shape, whereby the fatigue tester 10 may be rotated to various positions relative to the support member 44 (see generally FIGS. 2, 4 and 7). The compliance transducer 32 is mounted to a precision linear sliding micrometer 56 of known construction having a 9.0 cm travel with a vernier dial. The slide micrometer 56 is mounted to the base 46 of the support member 44.

The compliance transducer 32 provides a continuous indication of a selected tube's 18 dilation. The dilation can be mapped along the entire length of the tube 18, wherein the tube dilation can be used as a control feedback parameter to ensure that the prosthesis is subjected to a specific strain range. The compliance transducer 32 is preferably of the laser scanning micrometer type, known to those skilled in the art, with a diameter scanning range of 1 to 30 mm. One such laser scanning micrometer is available from Keyence Corporation of America, Woodcliff Lake, N.J.

The compliance transducer 32 is electrically coupled to the compliance transducer controller 16. The compliance transducer controller 16 has a digital light emitting diode (LED) display which visually indicates to the operator the dilation diameter being measured. The compliance transducer controller 16 is also coupled to the microprocessor-based controller 12 by electrical leads of known construction, wherein a proportional analog signal is transmitted to a data acquisition board (not shown) contained within the microprocessor-based controller 12 for direct processing by the computer.

Figure 5:
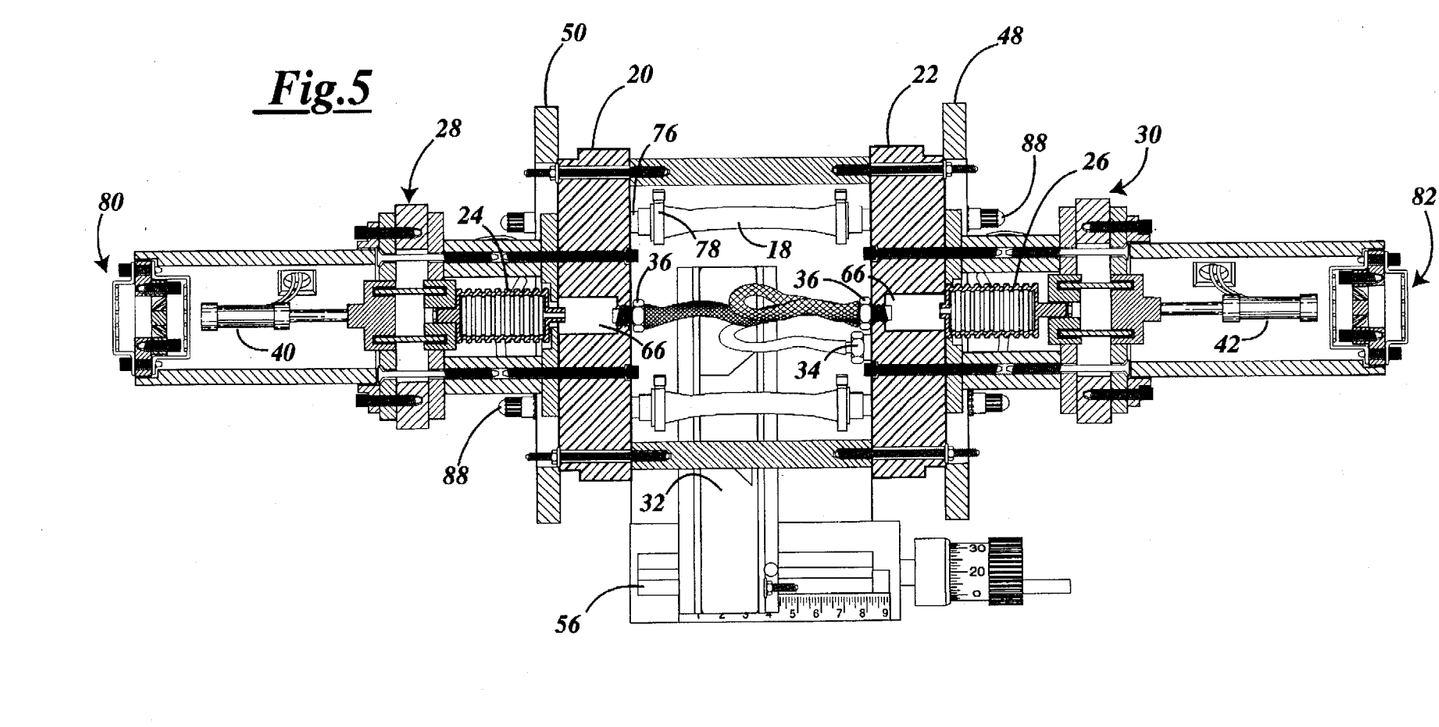
FIG. 5 is a partial sectional top plan view of the intravascular prosthesis fatigue tester of the type shown in FIG. 2.
Figure 6:
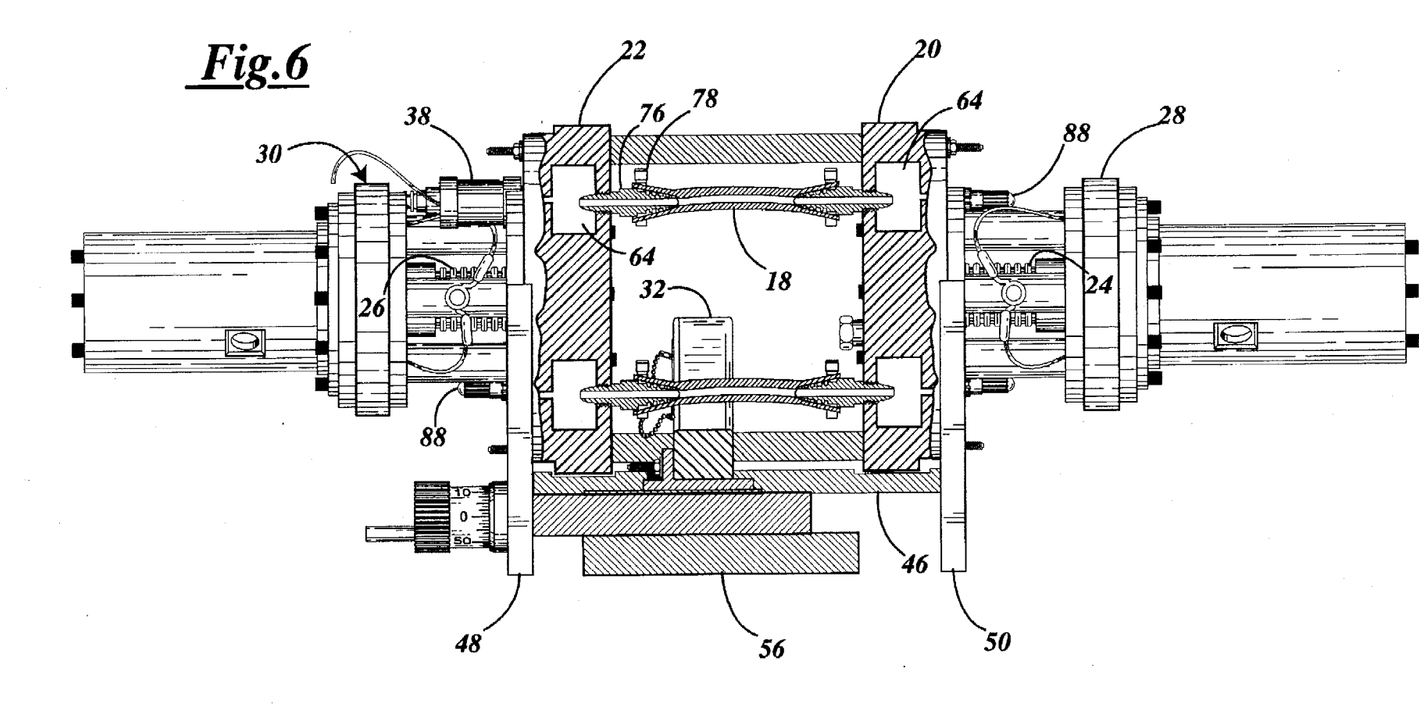
FIG. 6 is a partial sectional back elevational view of the intravascular prosthesis fatigue tester of the type shown in FIG. 2.

Referring now to FIGS. 4-6, the specific components of the fatigue tester 10 will be discussed. Without any limitation intended, the prosthesis containing tubes 18 are made from a flexible latex rubber having a hollow central axis or channel which open to first and second ends 58 and 60, thereby featuring compliance characteristics comparable to healthy in vitro implant conditions. A wide variety of implant conditions can be accommodated for testing prosthesis including grafts and stents, by varying independently the inner or outer diameters of the tube. In the preferred embodiment, the material and wall thicknesses are selected for a diameter expansion of 3-5% or 5-7%. The inner diameter of the tube 18 is such that a friction fit retains the desired prosthesis within the tube 18 (see FIG. 6).

The tube 18 is connected in-line to a fluid flow circuit of the fatigue tester 10. Generally, a continuous fluid conduit or passage is formed between bellows 24 and 26, manifolds 20 and 22, and tubes 18 (see FIGS. 5-7). When the bellows are compressed, decreasing the volume of the fluid conduit, the increased fluid pressure causes the tube 18 and prosthesis to expand. When the bellows 24 and 26 expand, the fluid pressure decreases allowing the tube 18 to contract. The bellows 24 and 26 are simultaneously compressed and expanded, to thereby force the fluid into the tubes 18 from each end of the tube 18. The bellows' 24 and 26 expansion and compression simulates within the tube 18, the systolic and diastolic flow of blood through a patients circulatory system. A fluid such as saline may be selected to simulate fluids encountered in vitro. The manifolds 20 and 22 are preferably constructed from a non-corrosive material such as polypropylene, polytetrafluroethylene, or stainless steel.

Referring to FIG. 7, those skilled in the art will appreciate that one or more tubes 18 may be coupled to the first and second manifolds 20 and 22, wherein radial bores in each manifold form a fluid passage 62 between a plurality of outlet passages 64 and a central longitudinal bore or inlet 66. The plurality of tubes 18 are sealably connected to corresponding outlet passages 64 and the bellows 24 and 26 are connected to the inlet 66 of the manifolds 20 and 22 respectively. The element 36 is sealably screwed into a longitudinal bore 68, which extends from an outer surface of the manifold and into the inlet 66. One method of forming the fluid passage 62 within each manifold 20 and 22 is to cut bores 70 from an outer side surface 72 of the manifold through outlet passages 64 and into the inlet 66, wherein the outer hole is plugged with a conventional plug 74.

Referring again to FIGS. 4–6, in the preferred embodiment, four tubes 18 are shown coupled to four outlets 64 of the manifolds 20 and 22, wherein the outlets 64 are radially spaced an equal distance from each other. The first end 58 of the tube 18 is connected to a conventional tube fitting 76. The fitting 76 is sealably attached to the outlet 64 of the first manifold 20. Likewise, the second end 60 of the tube 18 is connected to a conventional tube fitting 76 which is attached to an outlet 64 of the second manifold 22. The first and second ends 58 and 60 of tube 18 are held in place on fittings 76 by a conventional clamp 78. Those skilled in the art will appreciate that manifolds 20 and 22 may include more than four outlets to receive more than four tubes.

Referring to FIG. 5, one end of each bellows 24 and 26 is sealably attached to the inlet 66 of manifold 20 and 22 respectively, while the other end of each bellows 24 and 26 is sealably attached to a voice-coil drive motor 28 and 30 respectively. Cooling fans 80 and 82 are attached to motors 28 and 30 to remove excess heat from the system. The motors 28 and 30 are driven linearly fore and aft between a preset origin causing bellows 24 and 26 to expand and contract. Those skilled in the art will appreciate that the initial volume of the fluid conduit may be increased or decreased by changing the starting point or origin of the drive motors 28 and 30.

Linear displacement transducers 40 and 42 are coupled to both the drive motors 28 and 30 and microprocessor-based controller 12 such that the amplitude and frequency of the fluid being forced into the tubes 18 (the pulsating fluid) is monitored and controlled. The microprocessor-based controller 12 controls the fluid pulsations over a frequency range from 0 to over 6000 cycles per minute under closed loop control.

The pressure transducer 38 is coupled within the fluid conduit and linked to the microprocessor-based controller 12. Feedback signals from the linear displacement transducers 40 and 42 and the pressure transducer 38 provides the information necessary for the microprocessor 12 to adjust origin and rate of the drive motors 28 and 30 to thereby maintain the desired amplitude and frequency of the pulsating fluids.

In the preferred embodiment, the drive motors 28 and 30 and linear displacement transducers 40 and 42 are electrically coupled in parallel, to thereby simultaneously pulsate the fluids. Those skilled in the art will appreciate that the drive motors 28 and 30 and transducers 40 and 42 could be independently coupled to the microprocessor based controller 12, whereby the phase between the motors 28 and 30 and the frequency of each motor 28 and 30 could thereby be controlled independently. A power amplifier 84 is connected in series between the microprocessor 12 and linear drive motors 28 and 30 and converts an input drive signal from the microprocessor 12 to a voltage for driving the motors 28 and 30.

The microprocessor-based controller 12 uses a PID control algorithm for controlling the drive motors 28 and 30. The feedback signals from either the linear displacement transducers 40 and 42 or the pressure transducer 38 are amplified and then converted to a digital value by means of an internal analog to digital converter. Over time the resulting feedback value can be represented as a waveform. This waveform is then subtracted from a baseline or desired "command waveform". The resulting waveform or "error signal" is typically sinusoidal with respect to time if the "command waveform" is sinusoidal. Although the control of the motors based on the feedback signal may correspond to a displacement or pressure, displacement control is presently preferred, wherein the pressure feedback is used to monitor the integrity of the fluid conduit.

After the error signal is computed, the microprocessor then performs several mathematical operations on the error signal known as PID control. First, the error signal is multiplied by a scaler value $K_1$ to obtain a proportional (P) value. The error signal is also integrated over time and multiplied by scaler value $K_2$ to obtain an Integration (I) value. The error value is also differentiated with respect to time and multiplied by scaler value $K_3$ to obtain a differentiation (D) value. The P, I, and D values are then summed together and converted to a proportional drive output voltage by means of a digital to analog converter built into the microprocessor-based controller 12. Power amplifier 84 then converts this voltage to a current used to drive the linear voice coil motors 28 and 30. The PID control tends to reposition the origin of the linear drive motors 28 and 30 to minimize the error signal.

To further enhance the accuracy of the control loop and maintain the desired compliance or specimen dilation, the peak end levels of the feedback signal from the linear displacement or pressure transducers are monitored by the microprocessor based controller 12. If the peak end levels of the feedback signal vary from a predetermined peak level (ie: due to changing tube/stent compliance conditions, thermal changes in fluid media, etc.), the software automatically adjusts the command waveform used in the PID control until the desired feedback signal end level is achieved.

An additional feature of the microprocessor-based control system is it's ability to utilize the readings from the compliance measurement transducer to make constant corrections to the desired feedback signal end levels. This ensures that a constant specimen dilation amplitude is maintained. To accomplish this, the signal from the proportional voltage output of the compliance measurement transducer is converted to a digitized signal. This signal is then analyzed to determine values $D_{max}$ and $D_{min}$ associated with the maximum and minimum specimen diameters. The $D_{max}$ and $D_{min}$ values are then compared to predetermined optimal max and min values. The difference between the actual and desired diameter values are multiplied by a scaler $K_4$ and the resulting value is added to the desired feedback signal end level.

The pulsating fluids simulates the load conditions to which a prosthesis would be subjected. By pulsating the fluid within tubes 18 by means of the pumps, the diameter of a stent, for example, increases and decreases, thereby subjecting the device to fatigue stress/strains. The microprocessor-based controller 12 and fatigue tester 10 may also simulate heart beat rates from 0–100 beats per second, tube 18 compliances from 0–7% or vessel pressures from 1–1000 mm Hg.

In order to further simulate the physiological conditions on the prosthesis, the fluid within the fluid conduit is maintained at 37° C. A temperature transducer 34 and heating elements 36 are coupled within the fluid conduit and linked to a microprocessor-based temperature controller (not shown). A signal is sent from the temperature transducer 34 to the temperature controller, indicating the temperature of the fluid. When the temperature controller determines that the temperature of the fluid is below a minimum threshold level, the heating elements 36 are activated until the fluid's temperature rises above the threshold minimum.

The microprocessor-based temperature controller uses a PID control algorithm, whereby the temperature transducer 34 signal is compared to a desired setpoint value (typically 37° C). The difference or "error" is then scaled using a proportional (P) calculation, integrated over time and scaled using an Integration (I) calculation and differentiated with respect to time and scaled using a Differentiation (D) calculation. The temperature P, I, and D values are then summed together and the resulting value is used to drive a solid state relay using a Pulse Width Modulation (PWM) technique. The solid state relay activates the heating elements 36, when necessary, to maintain the fluid temperature at the desired temperature setpoint.

Figure 3:
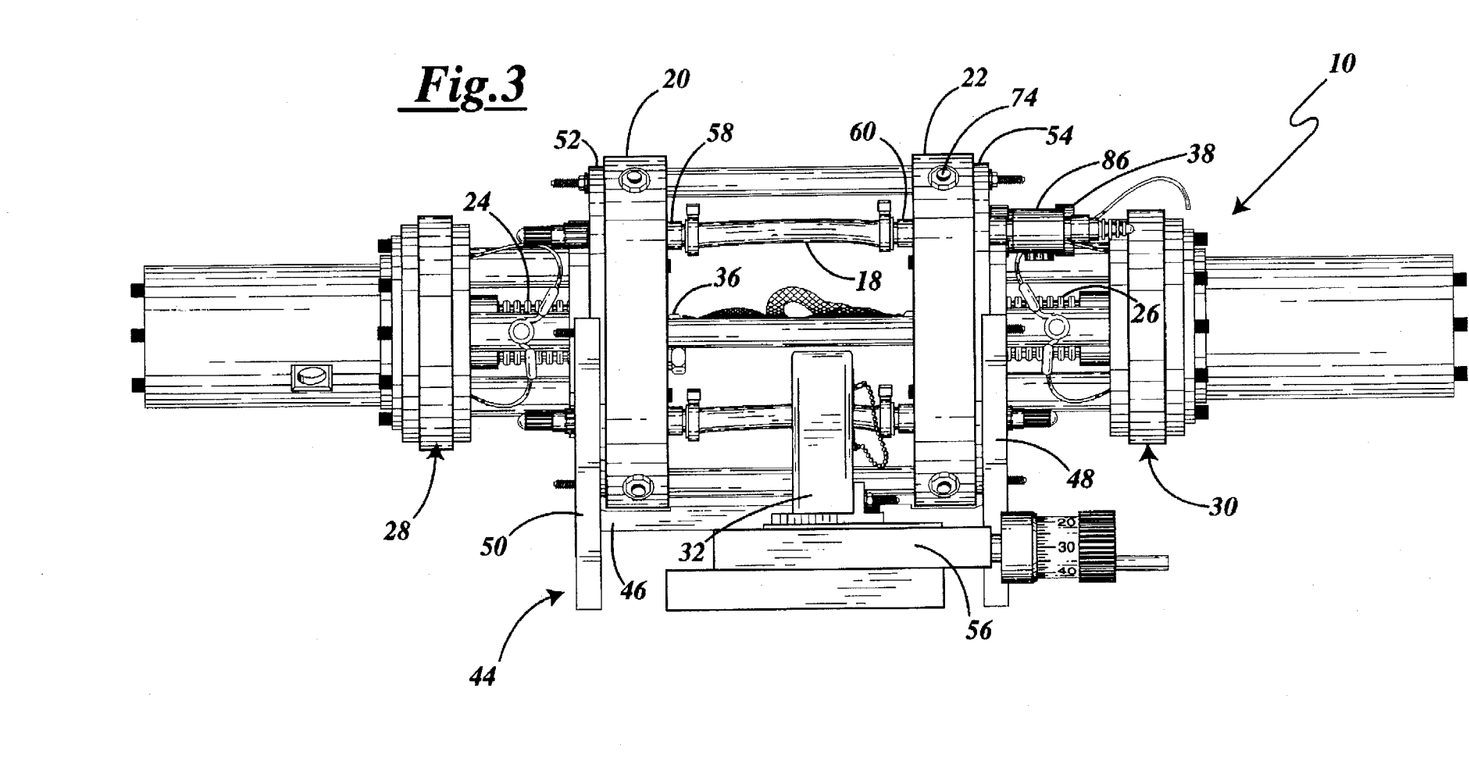
FIG. 3 is a front elevational view of the intravascular prosthesis fatigue tester of the type shown in FIG. 2.

Referring again to FIGS. 2 and 3, a fluid flow valve 86 is connected in-line to an outlet passage 64, allowing the fluid conduit to be filled or drained of a desired fluid (see FIG. 3). Fittings 88 are sealably attached to bores which extend from an outer end surface of the manifolds 20 and 22 and into the manifolds opposite each outlet passage 64 (see FIG. 5). The fittings 88 of known construction allow accessibility to the tubes 18 for a radial measurement device and specimen insertion.

Having described the constructional features of the present invention, the mode of use will now be discussed. The user inserts the prosthesis to be tested in tubes 18 through fittings 88. A fluid such as saline is filled into the outlet passages 64, manifolds 62, central passages 66, and tubes 18 through the fluid flow valve 86. The user then controls the amplitude and frequency of the linear driven pumps by selecting (using an associated personal computer and keyboard) the microprocessor-based controller's 12 mode of control (i.e.: heart beat simulation, tube 18 compliances, vessel pressure, etc.) and inputting the desired baseline parameters and command waveform for the test. The microprocessor-based controller 12 then controls the pressure, volume, pulse frequency and pulse amplitude within the fluid conduit through a servo mechanism type feedback and control. At various intervals during the testing, the user may remove and examine the prosthesis for structural integrity and compliance with standardized requirements. Alternatively, an endoscope assembly may be inserted through fittings 88 and into tubes 18 to inspect the prosthesis without removing it from the tubes 18.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A device for measuring compliance conditions of a prosthesis under simulated physiologic loading conditions, comprising:

a) a fluid conduit having a channel extending therethrough between a first and second end, wherein the channel is adapted for containing at least one prosthesis therein;

b) a first linear driven pump attached to the first end of said conduit and a second linear driven pump attached to the second end of said conduit, wherein said first and second linear driven pumps displace a fluid contained within said conduit;

c) a plurality of transducers coupled to said fluid conduit to thereby measure a plurality of predetermined conditions within said fluid conduit; and d) a microprocessor-based controller interconnected with said first and second linear driven pumps and said plurality of transducers, whereby the microprocessor-based controller adjusts a pulse frequency of the first and second linear driven pumps to thereby servo simulate physiologic loading conditions on the prosthesis within the fluid conduit.

2. The device as recited in claim 1, further comprising an uninterruptable power supply coupled to both said microprocessor-based controller and said first and second linear driven pumps.

3. The device as recited in claim 1, wherein said plurality of transducers are selected from the group consisting of a linear displacement transducer, a pressure transducer, and a compliance transducer.

4. The device as recited in claim 1, further including a linear displacement transducer coupled to said microprocessor-based controller and further coupled to one of said first and second linear driven pumps.

5. The device as recited in claim 1, further comprising a temperature transducer coupled to said fluid conduit and further coupled to a microprocessor-based temperature controller.

6. The device as recited in claim 1, wherein said first and second linear driven pumps include drive motors of the electrodynamic linear voice coil driven type.

7. The device as recited in claim 1, further including a compliance transducer aligned with at least one prosthesis contained in the channel of said fluid conduit, wherein said transducer provides compliance feedback.

8. The device as recited in claim 7, wherein said compliance transducer is electrically coupled to a compliance transducer controller which is coupled to said microprocessor based controller.

9. The device as recited in claim 7, wherein said compliance transducer is attached to a linear sliding micrometer which is coupled to the fluid conduit to thereby accurately position the compliance transducer with respect to the fluid conduit.

10. The device as recited in claim 1, further including a pressure transducer coupled to said microprocessor based controller and further coupled to said fluid conduit.

11. The device as recited in claim 1, further including a temperature maintenance means coupled to said microprocessor based controller and said fluid conduit for maintaining the fluid temperature within the fluid conduit at a desired temperature.

* * * * *